United States Patent
Li et al.

(10) Patent No.: US 9,050,353 B2
(45) Date of Patent: Jun. 9, 2015

(54) USE OF ICARIIN AND EPIMEDIUM FLAVONOIDS CONTAINING ICARIIN TO TREAT DISEASES ASSOCIATED WITH MYELIN SHEATH LESION

(75) Inventors: Lin Li, Beijing (CN); Linlin Yin, Beijing (CN); Lili Lin, Beijing (CN); Lan Zhang, Beijing (CN); Wen Wang, Beijing (CN); Ruyi Zhang, Beijing (CN)

(73) Assignee: Xuanwu Hospital of Capital Medical University, Beijing (CN)

( * ) Notice: Subject to any disclaimer, the term of this patent is extended or adjusted under 35 U.S.C. 154(b) by 125 days.

(21) Appl. No.: 13/703,168

(22) PCT Filed: Jun. 7, 2011

(86) PCT No.: PCT/CN2011/075374
§ 371 (c)(1),
(2), (4) Date: Feb. 26, 2013

(87) PCT Pub. No.: WO2011/153929
PCT Pub. Date: Dec. 15, 2011

(65) Prior Publication Data
US 2013/0157966 A1 Jun. 20, 2013

(30) Foreign Application Priority Data

Jun. 11, 2010 (CN) .......................... 2010 1 0198154

(51) Int. Cl.
*A61K 31/7048* (2006.01)
*A61K 36/296* (2006.01)

(52) U.S. Cl.
CPC .......... *A61K 31/7048* (2013.01); *A61K 36/296* (2013.01)

(58) Field of Classification Search
None
See application file for complete search history.

(56) References Cited

U.S. PATENT DOCUMENTS

2002/0013280 A1* 1/2002 Xin .................................. 514/27
2005/0220906 A1* 10/2005 Deng ............................. 424/759

FOREIGN PATENT DOCUMENTS

| CN | 101244074 A | 8/2008 | |
|---|---|---|---|
| CN | 101411810 A | 4/2009 | |
| CN | 101675986 A | 3/2010 | |
| CN | 101843629 A | 9/2010 | |
| WO | WO 2008089669 A1 * | 7/2008 | ............ A61K 36/296 |

OTHER PUBLICATIONS

Li, L. I., Zhou, Q. X., & Shi, J. S. (2005). Protective effects of icariin on neurons in. ured by cerebral ischemia/reperfusion. Chinese medical journal, 118(19), 1637-1643.*

Shields, D. C., Schaecher, K. E., Saido, T. C., & Banik, N. L. (1999). A putative mechanism of demyelination in multiple sclerosis by a proteolytic enzyme, calpain. Proceedings of the National Academy of Sciences, 96(20), 11486-11491.*

Hauser, S. L., & Goodkin, D. E. (2001). Multiple sclerosis and other demyelinating diseases. Harrisons Principles of Internal Medicine, 2, 2452-2461.*

Extended Supplementary Search Report for corresponding EP Application No. 11791920.9 mailed Nov. 12, 2013.

Hendriks, et al., "Flavonoids Inhibit Myelin Phagocytosis by Macrophages; a Structure-activity Relationship Study," Biochemical Pharmacology, Mar. 1, 2001, pp. 877-885, XP002715582.

Guo, et al., "Protective Effects of Icariin on Brain Dysfunction Induced by Lipopolysaccharide in Rats," Phytomedicine, Gustav Fischer Verlag, vol. 17, No. 12, Apr. 12, 2010, pp. 950-955, XP027286176.

Kang, et al., "Degeneration and Impaired Regeneration of Gray Matter Oligodendrocytes in Amyotrophic Lateral Sclerosis," Nature Neuroscience, vol. 16, No. 5, May 2013, pp. 571-579, XP002715583.

Office Action for corresponding European Appl. No. 11 791 920.9 dated Oct. 10, 2014.

* cited by examiner

Primary Examiner — Shaojia Anna Jiang
Assistant Examiner — Dale R Miller

(57) ABSTRACT

New use of icariin and Epimedium flavaoids containing icariin is provided by the present invention. Specifically, uses of compounds of Formula I or Epimedium containing compounds of formula I, Epimedium flavanoids, or extracts of Epimedium in manufacturing medicaments for treating, preventing, reducing and/or relieving diseases and/or conditoins related to neural myelin sheath impairments, or use of above materials in manufacturing medicaments for relieving demyelination and/or promoting repair of myelin sheath are provided by the present application, wherein, $R_1$ is selected from H, halogen, $-C_{1-6}$ alkyl, and $-C(O)-C_{1-4}$ alkyl

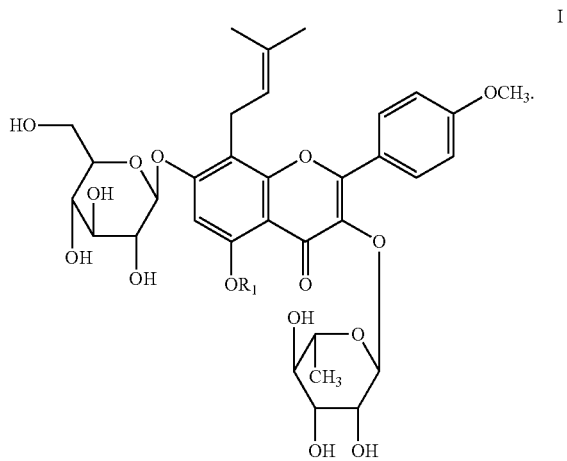

11 Claims, No Drawings

USE OF ICARIIN AND EPIMEDIUM FLAVONOIDS CONTAINING ICARIIN TO TREAT DISEASES ASSOCIATED WITH MYELIN SHEATH LESION

CROSS-REFERENCE TO RELATED APPLICATIONS

This application is a US national stage application of PCT/CN2011/075374 filed Jun. 7, 2011, which claims priority to Chinese Patent Application No. 201010198154.8, filed Jun. 11, 2010, the entireties of which are incorporated herein by reference.

TECHNICAL FIELD

The present invention belongs to field of pharmaceutical technology, relates to new uses of icariin and icariin-containing Epimedium flavanoids. Specifically, the present invention relates to a new use of icariin or icariin-containing Epimedium, Epimedium flavanoids or Epimedium extract, especially to a use of icariin or icariin-containing Epimedium, Epimedium flavanoids or Epimedium extract in the manufacture of a medicament for the prophylaxis and treatment of demyelinating diseases of nervous system.

BACKGROUND ART

Myelin sheath is a layer of lipid cell membrane that covers sheath nerve fiber axon outside and consists of myelin sheath cells, which main physiological function is to act "insulation" and protection functions on nerve axon, and facilitates rapid transmission of nervous impulses. Demyelinating disease is a group of disorders characterized by myelinoclasis of nerve fiber as main pathological change, which can either implicate central nervous system, or peripheral nervous system. This disease has main pathological features of: (1) nerve fiber myelinoclasis, presented in multiple small disseminated foci, or a relatively large focus formed by one or more foci in fusion; (2) demyelination lesions are distributed in alba, spinal cord or peripheral nerves, infiltrating in coatsleeve like form along inflammatory cells around veinlet. This kind of diseases include multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy, chronic inflammatory demyelinating polyneuropathy; and demyelinating diseases caused by other factors, including but not limited to leukoencephalopathy caused by ischemia-anoxia diseases, subacute combined degeneration caused by nutrition deficiency diseases, subacute sclerosing panencephalitis or progressive multifocal leukoencephalopathy caused by viral infection, diabetic neuropathy (this disease is mainly presented demyelination lesion), nervous lesions of systemic lupus erythematosus (this disease is mainly presented in demyelination lesion). The research of an effective drug for alleviating myelination and promoting myelin sheath plerosis may provide an important means for preventing demyelination diseases in central and peripheral nervous systems caused by various factors.

Epimedium is a perennial herb berberidaceae plant, and is a traditional Chinese medicine for reinforcing kidney. Epimedium extract or Epimedium flavanoids are main effective components of Epimedium. Epimedium flavanoids contain icariin, baohuoside, epimedin, in which icariin is a main active component thereof.

CONTENTS OF THE INVENTION

By wide and deep researches, the inventors surprisingly find icariin or icariin-containing Epimedium flavanoids have function of alleviating nervous system myelinoclasis and inflammatory cell infiltration, promoting formation and plerosis of myelin sheath, and can be used for manufacture of a medicament for prophylaxis and treatment of demyelinating disease in nervous system, and can be used for the treatment of diseases associated with nervous system myelin sheath lesions. Hence, the following invention is provided:

One aspect of the present invention relates to a compound of Formula I or a composition comprising a compound of Formula I, a use of Epimedium, Epimedium flavanoids, or Epimedium extract in the manufacture of a medicament for treatment, prophylaxis, alleviation and/or relief of diseases and/or disorders associated with nervous system myelin sheath lesions, or a use for the manufacture of a medicament for alleviating myelinoclasis and/or promoting myelin sheath plerosis:

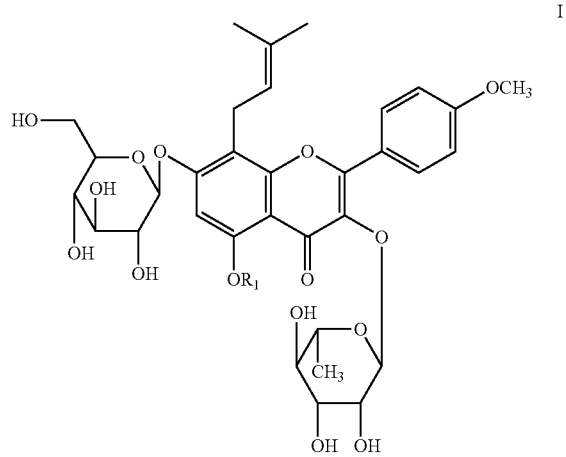

wherein, $R_1$ is selected from H, halogen, —$C_{1-6}$ alkyl, and —C(O)—$C_{1-4}$ alkyl.

The use according to any one of items of the present invention, the compound of Formula I is a compound of Formula Ia:

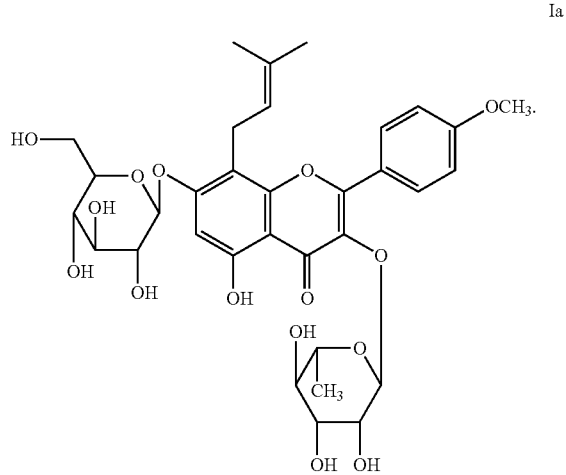

The use according to any one of items of the present invention is characterized by any one or more of the following items a) to e):

a) the composition comprises an effective amount of a compound of Formula I, Epimedium comprising a compound of Formula I, Epimedium flavanoids comprising a compound of Formula I, or Epimedium extract comprising a compound of Formula I, and optionally a pharmaceutically acceptable carrier;

b) the Epimedium, Epimedium flavanoids or Epimedium extract comprises therapeutically, prophylactically, alleviatively and/or relievedly effective amount of icariin;

c) the Epimedium, expressed in dry product, contains icariin ($C_{33}H_{40}O_{15}$) in an amount of not less than 0.5% (wt/wt), or not less than 1.0%, 2.0%, or 5.0%;

d) the Epimedium flavanoids contains icariin ($C_{33}H_{40}O_{15}$) in an amount of 20-90% (wt/wt), or 25-85%, 30-80%, 35-80%, 40-80%, 45-80%, 50-75%, 50-70%, 30-90%, 40-90%, 50-90%, 55-90%, or 60-90%;

e) the Epimedium flavanoids contains icariin ($C_{33}H_{40}O_{15}$) in an amount of 10-90% (wt/wt), or 15-85%, 20-80%, 25-80%, 30-80%, 35-80%, 40-75%, 40-70%, 20-90%, 30-90%, 40-90%, 50-90%, 55-90%, or 60-90%.

The use according to any one of items of the present invention is characterized by one or more of the following items a) to d):

a) the disease and/or disorder associated with nervous system myelin sheath lesion is a disease and/or disorder with myelin sheath lesion caused by various reasons;

b) the disease and/or disorder associated with nervous system myelin sheath lesion is a nervous system demyelinating disease;

c) the disease and/or disorder associated with nervous system myelin sheath lesion is selected from: multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy, and chronic inflammatory demyelinating polyneuropathy;

d) the disease and/or disorder associated with nervous system myelin sheath lesion is selected from: leukoencephalopathy caused by ischemia-anoxia diseases, subacute combined degeneration caused by nutrition deficiency diseases, subacute sclerosing panencephalitis caused by viral infection or progressive multifocal leukoencephalopathy, diabetic neuropathy, and systemic lupus eythematosus.

In one embodiment, the content of icariin in Epimedium flavanoids of the present invention is 40%-90%, for example about 50%, 55%, 60%, 65%, 70%, 75%, 80%, especially for example about 60%.

Another aspect of the present invention relates to a method for treatment, prophylaxis, alleviation and/or relief of a disease and/or disorder associated with nervous system myelin sheath lesion, comprising a step of administering a subject an effective amount of a compound of Formula I, or a composition, Epimedium, Epimedium flavanoids, or Epimedium extract containing a compound of Formula I.

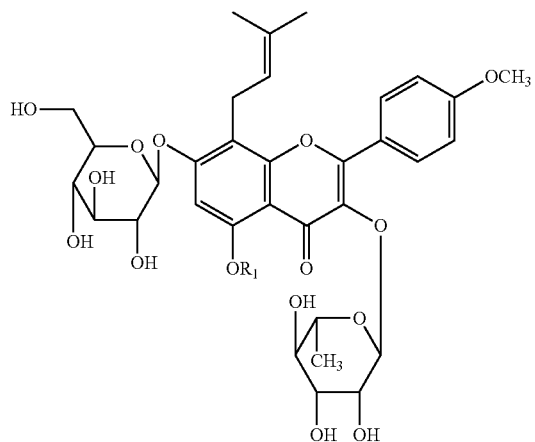

wherein, $R_1$ is selected from H, halogen, —$C_{1-6}$ alkyl, and —C(O)—$C_{1-4}$ alkyl.

The method according to any one of items of the present invention, the compound of Formula I is a compound of Formula Ia:

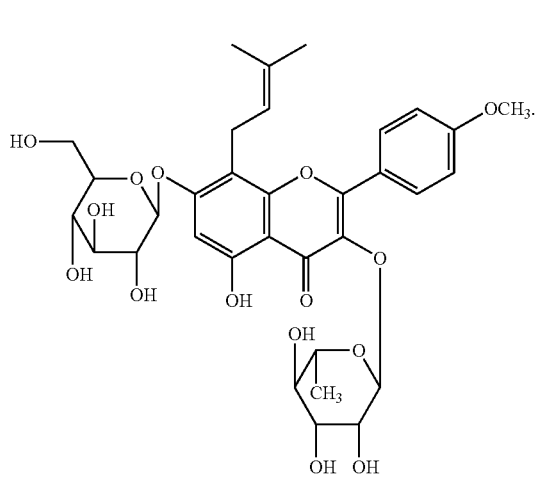

The method according to any one of items of the present invention is characterized by one or more of the following items a) to e):

a) the composition comprises an effective amount of a compound of Formula I,

Epimedium comprising a compound of Formula I, Epimedium flavanoids comprising a compound of Formula I, or Epimedium extract comprising a compound of Formula I, and optionally a pharmaceutically acceptable carrier;

b) the Epimedium, Epimedium flavanoids or Epimedium extract comprises therapeutically, prophylactically, alleviatively and/or relievedly effective amount of icariin;

c) the Epimedium, expressed in dry product, contains icariin ($C_{33}H_{40}O_{15}$) in an amount of not less than 0.5% (wt/wt), or not less than 1.0%, 2.0%, or 5.0%;

d) the Epimedium flavanoids contain icariin ($C_{33}H_{40}O_{15}$) in an amount of 20-90% (wt/wt), or 25-85%, 30-80%, 35-80%, 40-80%, 45-80%, 50-75%, 50-70%, 30-90%, 40-90%, 50-90%, 55-90%, or 60-90%;

e) the Epimedium flavanoids contain icariin ($C_{33}H_{40}O_{15}$) in an amount of 10-90% (wt/wt), or 15-85%, 20-80%, 25-80%, 30-80%, 35-80%, 40-75%, 40-70%, 20-90%, 30-90%, 40-90%, 50-90%, 55-90%, or 60-90%.

The method according to any one of items of the present invention is characterized by one or more of the following items a) to d):

a) the disease and/or disorder associated with nervous system myelin sheath lesion is a disease and/or disorder with myelin sheath lesion caused by various reasons;

b) the disease and/or disorder associated with nervous system myelin sheath lesion is a nervous system demyelinating disease;

c) the disease and/or disorder associated with nervous system myelin sheath lesion is selected from: multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy, and chronic inflammatory demyelinating polyneuropathy;

d) the disease and/or disorder associated with nervous system myelin sheath lesion is selected from: leukoencephalopathy caused by ischemia-anoxia diseases, subacute combined degeneration caused by nutrition deficiency diseases, subacute sclerosing panencephalitis caused by viral infection or progressive multifocal leukoencephalopathy, diabetic neuropathy, and systemic lupus eythematosus.

In one embodiment, the content of icariin in Epimedium flavanoids of the present invention is 40%-90%, for example about 50%, 55%, 60%, 65%, 70%, 75%, 80%, especially for example about 60%.

Icariin, Epimedium flavanoids, and Epimedium extract can be purchased from market, and products of Epimedium flavanoids and Epimedium extract with different contents of icariin are also commercially available. They can be used for alleviating nervous system myelinoclasis and inflammatory cell infiltration, inhibiting inflammatory reaction, combating oxidative stress, promoting the formation, regeneration and plerosis of myelin sheath, and regulating cell immunity; especially for the treatment of central and peripheral demyelinating diseases of nervous system caused by various reasons, including but not being limited to neuropathies such as multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy, chronic inflammatory demyelinating polyneuropathy, leukoencephalopathy caused by ischemia-anoxia diseases, subacute combined degeneration caused by nutrition deficiency diseases, subacute sclerosing panencephalitis caused by viral infection or progressive multifocal leukoencephalopathy, diabetic neuropathy, systemic lupus eythematosus. The present invention also is useful in prophylaxis of the above diseases.

The Epimedium flavanoids and/or icariin of the present invention can be processed with a pharmaceutically acceptable carrier according to conventional technology in the art to form a pharmaceutical composition or various conventional dosage forms, and can be administered in conventional manner. Suitable dose can be determined by a doctor according to property of disease, severity of disease, age and body weight of patient.

Hence, the present invention further relates to a use of an icariin analog for treatment of nervous diseases caused by various reasons and characterized by myelinoclasis. The icariin analog refers to a molecule having similarity with substantive structure of icariin, for example, a molecule formed by protecting its chemical group with a protecting group. For example, a derivative in which its 5-hydroxyl is substituted with $C_{1-6}$ alkyl or halogen, and an ester thereof formed with a pharmaceutically acceptable organic acid such as acetic or an inorganic acid such as hydrochloric acid. Suitable protecting groups are well known in the art. Those skilled in the art can easily synthesize a derivative in which 5-hydroxyl is substituted with the $R_1$ group of the present invention from icariin as precursor, and then exert its therapeutical effects. Hence, according to the contents as described in the context of the present invention, it can be expected that the derivative in which 5-hydroxyl is substituted with the $R_1$ group of the present invention can also have the pharmaceutical activity of the present invention.

The composition of the present invention is expected to be orally administered, although the administration can be performed via any suitable manners, such as intravenous, intranasal, intraperitoneal, subcutaneous, intramuscular, topical, suppository route or implantation (slowly releasing molecule).

The administration manner of the composition can be suitable for injection, such as sterile water solution and sterile powder for extemporizing sterile injection solution or dispersion.

A wide range of dose can be adopted, depending on patient, severity of disease, and route and medium for administration. In this kind of composition having therapeutical effects, the amount of active compound is to obtain a suitable dose. The preferred composition of the present invention is prepared so that oral dose unit form comprises about 0.01 μg to about 2000 mg of active compound. A suitable amount is between about 1.0 μg and about 1500 mg, between about 1 μg and about 1000 mg, and between about 10 μg and about 500 mg.

Main active component or component group in an effective amount together with a suitable pharmaceutically acceptable carrier are prepared in a dosage unit form for convenient and effective administration. One dosage unit form can contain for example the main active compound in an amount of 0.01 μg to about 2000 mg per 100 g. When expressed in proportion, the active compound is usually present in about 0.5 μg to about 2000 mg/ml of carrier. In the composition containing supplementary active component, the dose can be determined by referring to common dose and administration manner of the component. Or, the dose to be administered can be proposed in form of an amount per kilogram body weight. In this case, an amount of about 0.004 μg to about 1000 mg can be administered for per kilogram body weight. The preferable amount range as considered in the present invention is from 50 μg to 500 mg per kilogram bodyweight, or about 0.01 μg to about 500 mg or about 0.1 μg to about 250 mg per kilogram bodyweight.

In the present invention, icariin ($C_{33}H_{40}O_{15}$, systematic name is: 3-((6-deoxymannopyranosyl)oxy)-7-(glucopyranosyloxy)-5-hydroxy-2-(4-methoxyphenyl)-8-(3-methyl-2-butenyl)-4H-1-benzopyran-4-ketone; molecular weight: 676.65), structure is as follows:

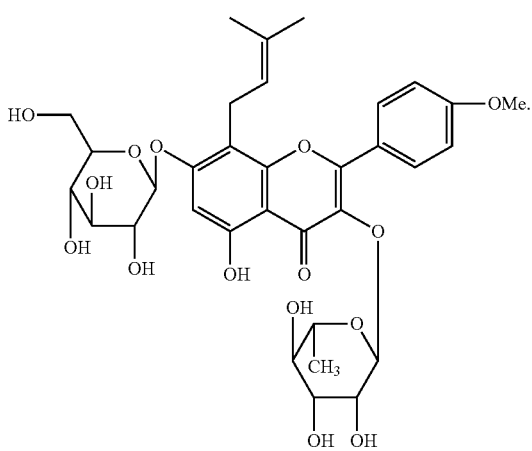

In the present invention, the term "Epimedium" meets the prescription of "Epimedium" of the Pharmacopoeia of the People' Republic of China, Edition 2005.

In the present invention, the term "Epimedium flavanoids" is main effective component of Epimedium, Epimedium flavanoids contain icariin, baohuoside, epimedin, in which icariin is the main active component thereof. In one embodiment, the "Epimedium flavanoids" also refers to an active component group containing (but not being limited to) the above effective components and being obtained by extracting Epimedium; hence, in one embodiment, the "Epimedium flavanoids" can also refer to Epimedium extract.

In the present invention, the term "Epimedium extract" refers to an extract obtained from Epimedium crude drug according to known methods, which may contain Epimedium flavanoids and main effective component icariin.

In the present invention, the term "halogen" refers to fluorine, chlorine, bromine, or iodine.

In the present invention, the term "$C_{1-6}$ alkyl" refers to a straight or branched alkyl group having 1 to 6 carbon atoms, and it can comprise its subsets such as $C_{1-5}$ alkyl, $C_{1-4}$ alkyl, $C_{1-3}$ alkyl, and may comprise its specific groups, such as methyl, ethyl, n-propyl, iso-propyl, n-butyl, iso-butyl, sec-butyl, tert-butyl, pentyl, hexyl.

In the present invention, the term "—C(O)—$C_{1-4}$ alkyl" refers to $C_{1-4}$ alkylacyl and their subsets such as —C(O)—$C_{1-3}$ alkyl, —C(O)—$C_{1-2}$ alkyl, and formyl group, acetyl, propionyl.

In the present invention, the term "effective amount" refers to an amount that can fulfill treatment, prophylaxis, alleviation and/or relief of the disease or disorder of the present invention, or fulfill alleviation of myelinoclasis and/or promotion of myelin sheath plerosis.

In the present invention, the effective amount of a compound of Formula I, or a Epimedium, Epimedium flavanoids, Epimedium extract, or composition comprising a compound of Formula I, is administrated to a subject per kilogram per day, in an amount of about 0.001 μg to about 1000 mg expressed in icariin. In one embodiment, the effective amount is about 0.01 μg to about 500 mg/kg/day, about 0.1 μg to about 250 mg/kg/day, about 1 μg to about 100 mg/kg/day, about 10 μg to about 100 mg/kg/day, about 50 μg to about 100 mg/kg/day, about 100 μg to about 100 mg/kg/day, about 1000 μg to about 50 mg/kg/day, about 50 μg to about 500 mg/kg/day, about 0.01 μg to about 500 mg/kg/day, or about 0.1 μg to about 250 mg/kg/day.

In the present invention, the term "composition" may further refers to a pharmaceutical composition, can be used for fulfilling treatment, prophylaxis, alleviation and/or relief of the disease or disorder of the present invention, or fulfill alleviation of myelinoclasis and/or promotion of myelin sheath plerosis in a subject.

In the present invention, the term "subject" can refer to a patient or other animals such as human, dog, monkey, cattle, horse that receives a compound of Formula I of the present invention or a Epimedium, Epimedium flavanoids, Epimedium extract, or composition comprising a compound of Formula I, for treatment, prophylaxis, alleviation and/or relief of the disease or disorder of the present invention, or for fulfilling alleviation of myelinoclasis and/or promotion of myelin sheath plerosis.

In the present invention, the term "disease and/or disorder" refers to a physical state of the subject, and this physical state is related to the disease and/or disorder of the present invention.

In the present invention, "%", if not specifically designated, refers to a weight/weight percentage.

In the present invention, the term "experimental autoimmune encephalomyelitis (EAE) animal model" is an important tool for studying several demyelinating diseases of nervous system in human, including EAE animal models induced by any conditions.

SPECIFIC MODELS FOR CARRYING OUT THE INVENTION

The present invention is described in details in conjunction with the following examples, but those skilled in the art would understand the following examples are merely used to illustrate the present invention, rather than to limit the scope of the present invention. The specific technologies or conditions that are not noted in the examples are performed according to the technologies or conditions as described in the documents or according to the specifications of the products. The used reagents or instruments without noted with manufacturers are all conventional products commercially available in market.

The materials and experimental methods used in the experiments of the present invention are generally and/or specifically described. Although many materials and operation methods used to fulfill the objective of the present invention are known in the art, they are still described in details as much as possible in the present invention. In the following examples, if not specifically noted, the Epimedium flavanoids contain 60% icariin are commercially available in market. In addition, in the following examples, if not specifically noted, the icariin purity is greater than 97% (expressed in $C_{33}H_{40}O_{15}$), and are commercially available in market.

EXAMPLE 1

Effects of Icariin on Nervous Function Damage in Experimental Autoimmune Encephalomyelitis (EAE) Mice Model Preparation of mice model and administration: experimental autoimmune encephalomyelitis (EAE) mice model is an important tool for studying various human demyelinating diseases of nervous system. In the present experiment, the preparation of EAE mice model was performed by immunizing female C57BL/6J mice with myelin sheath oligodendroglial cell surface glycoprotein $MOG_{35-55}$. That is, the mice were subcutaneously injected at dorsal part of spinal column with 0.2 mL of $MOG_{35-55}$ antigen elixir, and 0.2 ml of *bordetella pertussis* solution was intraperitoneally injected at the time of immunization injection and 48 h thereafter, respectively. Icariin was intragastrically administered after the last injection of *bordetella pertussis* solution, for consecutive 3 weeks.

Nervous function test method: the ethological changes of mice were observed by two experimenters every day using blind method. Scoring standard: 0 score, absence of symptom; 1 score, decrease of tail tension, evident slight gait awkward; 2 score, disappearance of tail tension, moderate gait abnormal, deficient in maintaining gesture; 3 score, limb strength weak; 4 score, limb paralysis; 5 score, near death or died.

Experimental results: after 8 days from immunization, the EAE model mice started to show motor dysfunction, which reached peak on about the $15^{th}$ day. Icariin had significant effects on reducing nervous function damage score in model animals (Table 1), which showed that icariin could facilitate the improvement of clinical symptoms, such as limb numbness, disequilibrium and paralysis, caused by diseases.

TABLE 1

Effects of icariin on nervous function damage in EAE mice model at peak of attack

| Group | Animal number | Nervous function damage score |
|---|---|---|
| Normal control | 15 | 0.00 ± 0.00 |
| EAE mode | 13 | 1.46 ± 0.50## |
| EAE + prednisone acetate (positive control drug) | 14 | 0.89 ± 0.28** |
| EAE + icariin 3 mg/kg | 15 | 0.57 ± 0.49** |
| EAE + icariin 10 mg/kg | 14 | 0.32 ± 0.52** |
| EAE + icariin 30 mg/kg | 15 | 0.13 ± 0.34** |

Average value ± SD;
$p < 0.01$, comparing model group with normal control group,
**$p < 0.01$, comparing drug group with model group.

EXAMPLE 2

Effects of Icariin on Nervous System Myelinoclasis in EAE Mice Model

Experimental objective: the myelinoclasis of myeloid tissue of EAE model mice were assayed by Luxol Fast Blue (LFB) staining, and the intervention effects of icariin on this pathological change were studied.

Experimental method: the mice were anesthetized with 10% chloral hydrate on the 29th day of experiment, fixed by perfusion of 4% paraformaldehyde, myeloid tissues were taken for making paraffin sections, section thickness 5 nm. Stained with LFB, observed under microscope, and scored according to the following standard: 0 score, absence of myelinoclasis; 1 score, one small range of myelinoclasis; 2 score, 2 or 3 small ranges of myelinoclasis; 3 score, 1 to 2 large ranges of myelinoclasis; 4 score, large ranges of myelinoclasis accumulatively existing in 20% or more of white matter regions.

Experimental results: obvious myelinoclasis was observed in spinal cord of EAE model mice, while the groups with administration of icariin had significantly alleviated myelinoclasis (Table 2), which indicated that icariin could be used for prophylaxis and treatment of demyelinating diseases of nervous system caused by various reasons.

TABLE 2

Effects of icariin on myeloid tissue myelinoclasis in EAE mice model

| Group | Animal number | Myelinoclasis (LFB staining score) |
|---|---|---|
| Normal control | 5 | 0.00 ± 0.00 |
| EAE model | 5 | 1.88 ± 0.31# |
| EAE + prednisone acetate (positive control drug) | 5 | 0.77 ± 0.22 |
| EAE + icariin 3 mg/kg | 5 | 0.91 ± 0.21** |
| EAE + icariin 10 mg/kg | 5 | 0.78 ± 0.16** |
| EAE + icariin 30 mg/kg | 5 | 0.66 ± 0.20** |

Average value ± SD;
$p < 0.01$, comparing model group with normal control group,
**$p < 0.01$, comparing drug group with model group.

EXAMPLE 3

Effects of Icariin on Inflammatory Cell Infiltration of Nervous System in EAE Mice Model Experimental objective: the pathological changes of spinal cord in EAE model, especially inflammatory cell infiltration situations was assayed by hematoxylin-eosin (HE) staining test, and the intervention effects of iridoids on these pathological changes were observed.

Experimental method: the mice were anesthetized with 10% chloral hydrate on the $28^{th}$ day of experiment, fixed by perfusion of 4% paraformaldehyde, spinal cord tissues were taken for making paraffin sections, section thickness 5 nm. Stained with HE, observed under microscope, and scored according to the following standard: 0 score, absence of cell infiltration; 1 score, spinal meninge cell infiltration; 2 score, 1 to 4 small ranges of cell infiltration around vessels; 3 score, 5 or more small ranges of cell infiltration around vessels, or one or more accumulatively substantial large range of cell infiltration; 4 score, a large number of cell infiltration ranges accumulatively existing in 20% or more of white matter regions.

Experimental results: EAE model mice had obvious inflammatory cell infiltration in spinal cord tissues, while the model mice administered with icariin had significantly reduced inflammatory cell infiltration (Table 3), which indicated that icariin could alleviate nerve inflammatory reaction, and facilitate the prevention and treatment of demyelinating diseases of nervous system.

TABLE 3

Effects of icariin on inflammatory cell infiltration in spinal cord tissues of EAE mice model

| Group | Animal number | Inflammatory cell infiltration (HE staining score) |
|---|---|---|
| Normal control | 3 | 0.00 ± 0.00 |
| EAE model | 3 | 2.17 ± 0.11## |
| EAE + prednisone acetate (positive control drug) | 3 | 1.05 ± 0.13** |
| EAE + icariin 3 mg/kg | 3 | 2.08 ± 0.09 |

TABLE 3-continued

Effects of icariin on inflammatory cell infiltration in
spinal cord tissues of EAE mice model

| Group | Animal number | Inflammatory cell infiltration (HE staining score) |
|---|---|---|
| EAE + icariin 10 mg/kg | 3 | 1.58 ± 0.16* |
| EAE + icariin 30 mg/kg | 3 | 1.18 ± 0.21** |

Average value ± SD;
p < 0.01, comparing model group with normal control group;
*P < 0.05,
**P < 0.01, comparing drug group with model group.

EXAMPLE 4

Effects of Icariin on Content of Serum Inflammatory Cytokines in EAE Mice Model

Experimental objective: interleukin-1 (IL-1) and IL-6 are important inflammatory cytokines, and have promoting effects on inflammatory reactions. This experiment used enzyme linked immunosorbent assay (ELISA) to measure contents of IL-1 and IL-6 in serums of EAE mice model, and the effects of icariin on these contents were observed.

Experimental method: mice were anesthetized with pentobarbital sodium, blood sample was taken from abdominal aorta, stood at room temperature for 2 h, centrifuged at 3000 rpm for 20 min, and supernatant was taken, stored at −80° C. for use. The operation was performed strictly according to the steps of specification of ELISA kit. Optical density was measured with ELIASA at 450 nm. The corresponding contents of IL-1 and IL-6 were calculated with the measured OD values on standard curves.

Experimental results: the mice of EAE model group had serum IL-1 and IL-6 contents significantly higher than those of normal control group; while icariin could reduce the contents of IL-1 and IL-6 in serum of the model mice (Table 4), which indicated that icariin could inhibit inflammatory reactions.

TABLE 4

Effects of icariin on contents of IL-1 and IL-6 in
serum of EAE mice model

| Group | Animal number | IL-1 content (pg/ml) | IL-6 content (pg/ml) |
|---|---|---|---|
| Normal control | 3 | 0.104 ± 0.002 | 0.128 ± 0.012 |
| EAE model | 3 | 0.130 ± 0.002## | 0.149 ± 0.011## |
| EAE + prednisone acetate (positive control drug) | 3 | 0.115 ± 0.001** | 0.121 ± 0.010** |
| EAE + icariin 3 mg/kg | 3 | 0.119 ± 0.003* | 0.147 ± 0.011 |
| EAE + icariin 10 mg/kg | 3 | 0.114 ± 0.001** | 0.142 ± 0.013 |
| EAE + icariin 30 mg/kg | 3 | 0.113 ± 0.002** | 0.126 ± 0.011** |

Average value ± SD;
p < 0.01, comparing model group with normal control group,
*P < 0.05,
**P < 0.01, comparing drug group with model group.

EXAMPLE 5

Effects of Icariin on Peripheral Blood T Cell Subgroup of EAE Mice Model

Experimental objective: one common feature of autoimmune diseases is the decrease of CD4+ T cells, and the increase of CD8+ T cells. In this experiment, the numbers of CD4+ and CD8+ cells in peripheral blood T cell subgroup of EAE mice mode were measured by flow cytometer (FACS), and the ratio of them was obtained; and the effects of icariin on these changes were observed.

Experimental method: mice were anesthetized with pentobarbital sodium, blood sample was taken from abdominal aorta, stood at room temperature for 2 h, centrifuged at 3000 rpm for 20 min, and cells were taken, added with anti-CD4+, CD8+ T cell antibodies with different markers, then the percentages of CD4+, CD8+ cells in T lymphocytes were measured by flow cytometer, and the CD4+/CD8+ T cells ratio was calculated.

Experimental results: in comparison with normal control group, the EAE model group mice had a significant decrease of peripheral blood CD4+ T cells, while a significant increase of CD8+ T cells, and a significant decrease of CD4+/CD8+ T cells ratio. Icariin could increase CD4+ T cells in peripheral blood of model mice, reduce CD8+ T cells, and elevate CD4+/CD8+ T cell ratio (Table 5). This indicated Icariin could regulate immunologic abnormality of T lymphocytes, normalize the CD4+/CD8+ T cells ratio, and thus could prevent or treat autoimmune diseases.

TABLE 5

Effects of icariin on peripheral blood T cell subgroup of EAE mice model

| Group | Animal number | CD4 + T cells (%) | CD8 + T cells (%) | CD4 +/CD8 + ratio |
|---|---|---|---|---|
| Normal control | 3 | 50.81 ± 6.62 | 37.48 ± 5.83 | 1.41 ± 0.51 |
| EAE model | 3 | 41.06 ± 4.32# | 51.73 ± 4.99# | 0.81 ± 0.19# |
| EAE + prednisone acetate (positive control drug) | 3 | 30.45 ± 8.77 | 60.62 ± 5.58 | 0.52 ± 0.23 |
| EAE + icariin 3 mg/kg | 3 | 52.78 ± 3.30 | 42.61 ± 3.10 | 1.25 ± 0.20 |
| EAE + icariin 10 mg/kg | 3 | 58.89 ± 1.27* | 36.43 ± 0.38* | 1.62 ± 0.06* |
| EAE + icariin 30 mg/kg | 3 | 55.81 ± 1.41 | 40.20 ± 1.79 | 1.39 ± 0.12* |

Average value ± SD;
P < 0.05, comparing model group with normal control group,
*P < 0.05, comparing drug group with model group.

EXAMPLE 6

Effects of Icariin on Content of Oligodendroglial Cells of Nervous System in EAE Mice Model Experimental objective: myelin sheath is formed with prominences of oligodendroglial cells. CNPase, myelin basic protein (MBP) are marker proteins of mature oligodendroglial cells. The present experiment was to observe the expression of CNPase and MBP to represent the content of oligodendroglial cells in spinal cord of EAE model mice by Western blot method; and to study the effects of icariin on it.

Experimental method: the mice were anesthetized and sacrificed, fresh spinal cord was taken on ice, total protein was extracted by cleavage on ice, to prepare Western blot sample, added separately with CNPase, MBP primary antibodies and incubated, added with corresponding secondary antibodies, ECL colorated, Kodak film exposed. Pictures were analyzed with Image J software and standardized with β-actin.

Experimental results: in comparison with control group, EAE model mice spinal cord CNPase, MBP bands became significantly narrow, integration grey level significantly decreased, which suggested the reduction of oligodendroglial cell number; while in the mice of icariin groups, CNPase, MBP bands became wide, and integration grey level increased significantly (Table 6). This indicated that icariin could significantly increase the number of oligodendroglial cells, facilitate the secretion and formation of myelin sheath, and thus could prevent or treat demyelinating diseases of nervous system.

TABLE 6

Effects of icariin on content of spinal cord oligodendroglial cells in EAE micemodel

| Group | Animal number | CNPase/actin Integration grey level | MBP/actin Integration grey level |
|---|---|---|---|
| Normal control | 3 | 1.25 ± 0.03 | 1.10 ± 0.05 |
| EAE model | 3 | 0.91 ± 0.05## | 0.88 ± 0.08## |
| EAE + prednisone acetate (positive control drug) | 3 | 1.20 ± 0.01** | 1.05 ± 0.11* |
| EAE + icariin 3 mg/kg | 3 | 1.16 ± 0.04** | 0.98 ± 0.13 |
| EAE + icariin 10 mg/kg | 3 | 1.28 ± 0.07** | 1.07 ± 0.08* |
| EAE + icariin 30 mg/kg | 3 | 1.33 ± 0.05** | 1.11 ± 0.06** |

Average value ± SD;
P < 0.05, comparing model group with normal control group,
*P < 0.05, comparing drug group with model group.

EXAMPLE 7

Effects of Epimedium Flavanoids on Nervous Function Damage in Experimental Autoimmune Encephalomyelitis (EAE) Rat Model Preparation of rat model and administration: experimental autoimmune encephalomyelitis (EAE) model is an important tool for studying various human demyelinating diseases of nervous system. In the example, the preparation of EAE rat model was performed by multipoint immunizing female Lewis rats subcutaneously at tail root with a homogenate of spinal cord and cerebral gray matter of Guinea pig as well as complete Freund's adjuvant after emulsification. They were intragastrically administered with Epimedium flavanoids for 3 weeks.

Nervous function test method: the ethological changes of rats were observed by two experimenters using blind method every day. Nervous function damage scoring standard: 0 score, absence of symptom; 1 score, decrease of tail tension, visible evident slight gait awkward; 2 score, double hind limbs weak, walk difficult; 3 score, double hind limbs paralysis; 4 score, double hind limbs paralysis and fore limbs weak; 5 score, four limbs paralysis; 6 score, near death or died.

Experimental results: on the $8^{th}$ day from immunization, the EAE rat models started to show motor dysfunction, which reached peak on the $12^{th}$ day. Epimedium flavanoids had significant effects on reducing nervous function damage score in model animals (Table 7), which indicated that Epimedium flavanoids could facilitate the improvement of clinical symptoms, such as limb numbness, disequilibrium and paralysis, caused by diseases.

TABLE 7

Effects of Epimedium flavanoids on nervous function damage in EAE rat model at peak of attack

| Group | Animal number | Nervous function damage score |
|---|---|---|
| Normal control | 6 | 0.00 ± 0.00 |
| EAE model | 7 | 3.07 ± 0.54## |
| EAE + prednisone acetate (positive control drug) | 6 | 0.83 ± 0.48** |
| EAE + Epimedium flavanoids 20 mg/kg | 6 | 2.17 ± 0.40 |
| EAE + Epimedium flavanoids 60 mg/kg | 6 | 1.58 ± 0.37* |

Average value ± SD;
P < 0.01, comparing model group with normal control group;
*P < 0.05,
**P < 0.01, comparing drug group with model group. "Normal control", in the text, if not designated otherwise, which refers to normal animal group that were not subjected to EAE treatment, neither were given an active substance.

EXAMPLE 8

Effects of Epimedium Flavanoids on Nervous System Myelinoclasis and Inflammatory Cell Infiltration in EAE Rat Model Experimental objective: in the example, the myelinoclasis of myeloid tissue in EAE rat model were assayed by Luxol Fast Blue (LFB) staining; the pathological changes of spinal cord in EAE rat models, especially inflammatory cell infiltration situations were observed by hematoxylin-eosin (HE) staining test; and the intervention effects of Epimedium flavanoids on the above pathological changes were studied.

Experimental method: the rats were anesthetized with 10% chloral hydrate on the $14^{th}$ day of experiment, fixed by perfusion of 4% paraformaldehyde, spinal cord tissues were taken for making paraffin sections, section thickness 4 μm. (1) Stained with LFB, observed under microscope, and scored according to the following standard: 0 score, absence of myelinoclasis; 1 score, one small range of myelinoclasis; 2 score, 2 or 3 small ranges of myelinoclasis; 3 score, 1 to 2 large ranges of myelinoclasis; 4 score, large ranges of myelinoclasis accumulatively existing in 20% or more of white matter regions. (2) Stained with HE, observed under microscope, and scored according to the following standard: 0 score, absence of cell infiltration; 1 score, spinal meninge cell infiltration; 2 score, 1 to 4 small ranges of cell infiltration around vessels; 3 score, 5 or more small ranges of cell infiltration around vessels, or one or more accumulatively substantial large range of cell infiltration; 4 score, a large number of cell infiltration ranges accumulatively existing in 20% or more of white matter regions.

Experimental results: in morphology, the spinal cord lumbar intumescentia and brain slice HE staining results of EAE model group rats showed there were a lot of inflammatory cell infiltration around small vessels; LFB myelin staining results showed lamellar demyelinating areas with different sizes; it could be observed under electron microscope that the foci had myelinoclasis, and vessels, neurons, axonal injuries as well. Epimedium flavanoids could alleviate pathological changes such as spinal cord lumbar intumescentia and brain substantive inflammatory cell infiltration as well as myelinoclasis of EAE model group rats, protect neurons, normal structure of oligodendroglial cells, and inhibit abnormal activation of astrocytes in model rats (Table 8). This indicated that Epimedium flavanoids could be used for prophylaxis and treatment of nervous system diseases with myelin sheath lesions caused by various reasons.

TABLE 8

Effects of Epimedium flavanoids on staining score of spinal cord lumbar intumescentia of EAE model group rats

| Group | Animal number | Myelinoclasis (LFB staining score) | Inflammatory cell infiltration (HE staining score) |
|---|---|---|---|
| Normal control | 3 | 0.00 ± 0.00 | 0.00 ± 0.00 |
| EAE model | 3 | 1.67 ± 0.33## | 2.89 ± 0.31## |
| EAE + prednisone acetate (positive control drug) | 3 | 0.89 ± 0.20** | 1.00 ± 0.29** |
| EAE + Epimedium flavanoids 20 mg/kg | 3 | 0.78 ± 0.22** | 1.56 ± 0.18** |
| EAE + Epimedium flavanoids 60 mg/kg | 3 | 0.56 ± 0.24** | 0.89 ± 0.26** |

Average value ± SD;
P < 0.01, comparing model group with normal control group,
**P < 0.01, comparing drug group with model group.

EXAMPLE 9

Effects of Epimedium Flavanoids on Content of Inflammatory Cytokines IL-1β in EAE Rat Model Experimental objective: interleukin 1β (IL-1β) is an important inflammatory cytokines, and has promoting effects on inflammatory reactions. This experiment used immunohistochemical method to measure the content of IL-1β in spinal cord lumbar intumescentia of EAE model group rat, and observed the effects of Epimedium flavanoids on the content.

Experimental method: rats were anesthetized with 10% chloral hydrate, fixed by perfusion of 4% paraformaldehyde, spinal cord tissue was taken for making frozen section. Incubated with IL-1β primary antibody, added with corresponding secondary antibody, third antibody, DAB developed, observed under microscope. Pictures were analyzed by Image Pro plus 5.0 software.

Experimental results: the number of IL-1β positive cells in spinal cord lumbar intumescentia of EAE model group rat was significantly higher than that of the normal control group, and had deep color in cell staining; while Epimedium flavanoids could reduce the number of IL-1β positive cells in model rats, and staining slight (Table 9). This indicated that Epimedium flavanoids could significantly inhibit the generation of nervous system inflammatory cytokines IL-1β, and facilitate the inhibition of neuroinflammation reaction.

TABLE 9

Effects of Epimedium flavanoids on IL-1β content of spinal cord lumbar intumescentia of EAE model group rats

| Group | Animal number | IL-1β Positive cell number | IL-1β Accumulative optical density (×10³) |
|---|---|---|---|
| Normal control | 3 | 279 ± 29 | 47.1 ± 5.0 |
| EAE model | 3 | 814 ± 67## | 136.8 ± 11.3## |
| EAE + prednisone acetate (positive control drug) | 3 | 672 ± 48* | 115.5 ± 8.6 |
| EAE + Epimedium flavanoids 20 mg/kg | 3 | 630 ± 50** | 105.0 ± 9.1** |
| EAE + Epimedium flavanoids 60 mg/kg | 3 | 460 ± 35** | 72.9 ± 6.2** |

Average value ± SD;
P < 0.01, comparing model group with normal control group,
*P < 0.05,
**P < 0.01, comparing drug group with model group.

EXAMPLE 10

Epimedium Flavanoids on Inflammatory Cytokines TNF-α Content in EAE Rat Models

Experimental objective: tumor necrosis factor α (TNF-α) is an important inflammatory cytokines, and has promoting effects on inflammatory reactions. This experiment used enzyme linked immunosorbent assay (ELISA) to measure TNF-α content of cerebral cortex in EAE rat model, and observe the effects of Epimedium flavanoids on the content.

Experimental method: rats were anesthetized and sacrificed, fresh brain tissues were was taken, processed to form cerebral cortex homogenate. The operation was performed strictly according to the steps of specification of ELISA kit. Optical density was measured with ELISA at 450 nm. The corresponding TNF-α content was calculated with the measured OD values on standard curve.

Experimental results: the TNF-α contents of cerebral cortex of EAE model group rats were significantly higher than that of the normal control group; while Epimedium flavanoids could reduce TNF-α contents of cerebral cortex of the model rats (Table 10), which indicated that Epimedium flavanoids could reduce inflammatory cytokines, and facilitate the inhibition of neuroinflammation reaction.

TABLE 10

Effects of Epimedium flavanoids on TNF-α content of cerebral cortex in EAE rat models

| Group | Animal number | TNF-α content (pg/mg pro) |
|---|---|---|
| Normal control | 3 | 31.29 ± 4.55 |
| EAE model | 4 | 160.99 ± 16.05## |
| EAE + prednisone acetate (positive control drug) | 3 | 64.29 ± 7.52** |
| EAE + Epimedium flavanoids 20 mg/kg | 3 | 103.98 ± 14.4** |
| EAE + Epimedium flavanoids 60 mg/kg | 3 | 67.86 ± 11.08** |

Average value ± SD;
P < 0.01, comparing model group with normal control group,
**P < 0.01, comparing drug group with model group.

EXAMPLE 11

Effects of Epimedium Flavanoids on NO Content and NOS Activity of Cerebral Cortex in EAE Rat Model Experimental objective: nitric-oxide synthase (NOS) catalyzes the generation of nitric oxide (NO). During inflammatory reaction, the activity of induced NOS increases, excess NO are generated and oxygen radicals are generated via oxidation, which may result in damages in nerve cells and myelin sheath. In this experiment, NOS activity and NO content were measured using biochemical kits in cerebral cortex of EAE rat model, and the effects of Epimedium flavanoids on changes thereof were observed.

Experimental methods: rats were anesthetized and sacrificed, fresh brain tissues were taken, weighed and mixed homogeneously with saline in a ratio of 1:10, and processed in ice-bath to form a brain homogenate, centrifuged at 10000 rpm for 10 min, supernatant was taken, treated with boiling-water-bath for 3 min, centrifuged at 10000 rpm for 5 min, 0.1 ml of supernatant was taken. The operation was strictly performed according to the kit specification as provided by Nanjing Jiancheng Bioengineering Institute.

Experimental results: EAE model group rats had cerebral cortex NOS activity and NO content significantly higher than those of normal control group; while Epimedium flavanoids could inhibit NOS activity and reduce NO content of cerebral cortex in model rats (Table 11). This indicated that Epimedium flavanoids could alleviate pathological lesions of nerve cells and myelin sheath via inhibiting NOS activity and reducing NO secretion.

TABLE 11

Effects of Epimedium flavanoids on NOS activity and NO content of cerebral cortex in EAE rat model

| Group | Animal number | NOS activity (U/mg protein) | NO content (mmol/mg protein) |
|---|---|---|---|
| Normal control | 6 | 2.40 ± 0.05 | 0.64 ± 0.30 |
| EAE model | 7 | 2.79 ± 0.01## | 2.10 ± 0.19## |
| EAE + prednisone acetate (positive control drug) | 6 | 2.44 ± 0.08** | 0.77 ± 0.01** |
| EAE + Epimedium flavanoids 20 mg/kg | 6 | 2.46 ± 0.07** | 0.78 ± 0.14** |
| EAE + Epimedium flavanoids 60 mg/kg | 6 | 2.35 ± 0.03** | 0.53 ± 0.30** |

Average value ± SD;
$P < 0.01$, comparing model group with normal control group,
**$P < 0.01$, comparing drug group with model group.

EXAMPLE 12

Effects of Epimedium Flavanoids on Oxidative Stress of Nervous System in EAE Rat Model Experimental objective: the lipid peroxidation between oxygen free radicals and unsaturated fatty acids of cell membranes and organelle membranes results in the damage, degradation, denaturation and dysfunction of membrane phospholipids. Malondialdehyde (MDA) is a metabolic product of lipid peroxidation, and the increase of MDA indicates the enhancement of lipid peroxidation, which may lead to damage of nerve cells and myelin sheath. Superoxide dismutase (SOD) can scavenge superoxide anions and is an important antioxidase in vivo. In this experiment, SOD activity and MDA content of brain tissues in EAE rat model were measured by biochemistry method, and the effects of Epimedium flavanoids on changes thereof were observed.

Experimental methods: rats were anesthetized and sacrificed, fresh brain tissues were taken, weighed and mixed homogeneously with saline in a ratio of 1:10 and processed in ice-bath to form a brain homogenate, centrifuged at 10000 rpm for 10 min, supernatant was taken, treated with boiling-water-bath for 3 min, centrifuged at 10000 rpm for 5 min, 0.1 ml of supernatant was taken. The SOD activity and MDA content were measured strictly according to the biochemical kits as provided by Nanjing Jiancheng Bioengineering Institute.

Experimental results: in comparison with normal control rats, the EAE model group rats had a significant decrease in SOD activity, and a significant increase in MDA content; while Epimedium flavanoids could significantly increase SOD activity and reduce MDA content of cerebral cortex in model rats (Table 12). This indicated that Epimedium flavanoids could enhance antioxidation ability, inhibit lipid peroxidation and facilitate protection of nerve cells and myelin sheath.

TABLE 12

Effects of Epimedium flavanoids on SOD activity and MDA content cerebral cortex in EAE rat model

| Group | Animal number | SOD activity (U/mg protein) | MDA content (nmol/mg protein) |
|---|---|---|---|
| Normal control | 6 | 136.0 ± 5.6 | 1.20 ± 0.06 |
| EAE model | 7 | 118.3 ± 3.6# | 1.50 ± 0.09# |
| EAE + prednisone acetate (positive control drug) | 6 | 134.5 ± 5.1 | 1.03 ± 0.09* |
| EAE + Epimedium flavanoids 20 mg/kg | 6 | 122.7 ± 7.2 | 1.11 ± 0.22* |
| EAE + Epimedium flavanoids 60 mg/kg | 6 | 142.9 ± 4.4** | 0.99 ± 0.03* |

Average value ± SD;
$P < 0.05$, comparing model group with normal control group,
*$P < 0.05$,
**$P < 0.01$, comparing drug group with model group.

EXAMPLE 13

Effects of Epimedium Flavanoids on Content of Oligodendroglial Cells of Nervous System in EAE Rat Model Experimental objective: myelin sheath is formed with prominences of oligodendroglial cells. 2'3'-cyclic adenosine monophosphate-3'-phosphodiesterase (CNPase) is a marker protein of mature oligodendroglial cells. In this experiment, CNPase content of cerebral cortex in EAE rat model was measured by Western blot method, CNPase content of spinal cord lumbar intumescentia was measured by immunohistochemical method; and the effects of Epimedium flavanoids on these contents were observed.

(1) Cerebral Cortex CNPase Content as Measured by Western Blot Method

Experimental method: rats were anesthetized and sacrificed, cerebral cortex was taken, total protein was extracted by ice cleavage for making Western blot sample, added with CNPase primary antibody and incubated, added with corresponding secondary antibody, ECL colorated, Kodak film exposed. Pictures were analyzed by Image J software and standardized with β-actin (as internal reference).

Experimental results: in comparison with control group, the cerebral cortex CNPase bands in EAE rat model became significantly narrow, integration grey level significantly decreased, which suggested the reduction of oligodendroglial cell number; while in the rats of Epimedium flavanoids groups, CNPase bands became wide, and integration grey level increased significantly (Table 13). This indicated that Epimedium flavanoids could significantly increase the number of oligodendroglial cells, facilitate the formation of myelin sheath.

TABLE 13

Effects of Epimedium flavanoids on content of cerebral cortex oligodendroglial cells in EAE rat model

| Group | Animal number | CNPase/actin integration grey level |
|---|---|---|
| Normal control | 3 | 1.61 ± 0.05 |
| EAE model | 3 | 0.83 ± 0.10## |
| EAE + prednisone acetate (positive control drug) | 3 | 1.33 ± 0.06** |
| EAE + Epimedium flavanoids 20 mg/kg | 3 | 1.26 ± 0.04** |
| EAE + Epimedium flavanoids 60 mg/kg | 3 | 1.34 ± 0.02** |

Average value ± SD;
P < 0.01, comparing model group with normal control group,
**P < 0.01, comparing drug group with model group.

(2) CNPase Content of Spinal Cord Lumbar Intumescentia as Measured by Immunohistochemical Method Experimental method: the rats were anesthetized with 10% chloral hydrate on the 14$^{th}$ day of experiment, fixed by perfusion of 4% paraformaldehyde, spinal cord tissues were taken for frozen section. Incubated with CNPase primary antibody, added with corresponding secondary antibody and third antibody, observed under microscope. Pictures were analyzed using Image Pro plus5.0 software to count positive cells.

Experimental results: in comparison with normal control group, the CNPase positive cells number of spinal cord lumbar intumescentia in EAE rat model decreased significantly, which indicated the reduction of number of oligodendroglial cells; while the number of CNPase positive cells of Epimedium flavanoids groups increased significantly (Table 14), which indicated that Epimedium flavanoids could increase oligodendroglial cells and facilitate the formation of myelin sheath.

TABLE 14

Effects of Epimedium flavanoids on number of oligodendroglial cells of spinal cord lumbar intumescentia in EAE rat model

| Group | Animal number | CNPase positive cell count |
|---|---|---|
| Normal control | 3 | 1840.0 ± 175.1 |
| EAE model | 3 | 872.1 ± 89.4## |
| EAE + prednisone acetate (positive control drug) | 3 | 1378.2 ± 125.4* |
| EAE + Epimedium flavanoids 20 mg/kg | 3 | 1535.5 ± 65.4** |
| EAE + Epimedium flavanoids 60 mg/kg | 3 | 2181.6 ± 212.0** |

Average value ± SD;
P < 0.01, comparing model group with normal control group,
*P < 0.05,
**P < 0.01, comparing drug group with model group.

EXAMPLE 14

Effects of Epimedium Flavanoids on Nerve Growth Factor Content in EAE Rat Model

Experimental objective: neurotrophic factors are important substances for constituting nerve regeneration microenvironment. Nerve growth factors (NGF) are important neurotrophic factors, can promote the regeneration and plerosis of nerve cells and myelin sheath. In this experiment, NGF content of spinal cord lumbar intumescentia in EAE rat model was measured by immunohistochemical method, and the effects of Epimedium flavanoids on the content was observed.

Experimental method: the rats were anesthetized with 10% chloral hydrate, fixed by perfusion of 4% paraformaldehyde, spinal cord tissues were taken for frozen section. Incubated with NGF primary antibody, added with corresponding secondary antibody and third antibody, DAB colorated, observed under microscope, and pictures were analyzed using Image Pro plus5.0 software.

Experimental results: the analysis of integrated optical density (IOD) of picture via software showed the NGF positive cells number of spinal cord lumbar intumescentia in EAE rat model group was significantly lower than that of the normal control group; while the expression of NGF of Epimedium flavanoids groups increased significantly, and cell coloration was darker (Table 15), which indicated that Epimedium flavanoids could significantly increase NGF generation and secretion in nervous system, and facilitate the formation and plerosis of nerve cells and myelin sheath.

TABLE 15

Effects of Epimedium flavanoids on NGF expression of spinal cord lumbar intumescentia in EAE rat model

| Group | Animal number | NGF positive cell Accumulative optical density (×10$^5$) |
|---|---|---|
| Normal control | 3 | 13.32 ± 0.05 |
| EAE model | 3 | 6.41 ± 1.33## |
| EAE + prednisone acetate (positive control drug) | 3 | 11.25 ± 1.67* |
| EAE + Epimedium flavanoids 20 mg/kg | 3 | 11.46 ± 0.88* |
| EAE + Epimedium flavanoids 60 mg/kg | 3 | 13.56 ± 1.51** |

Average value ± SD;
P < 0.01, comparing model group with normal control group,
*P < 0.05,
**P < 0.01, comparing drug group with model group.

EXAMPLE 15

Effects of Epimedium Flavanoids on Brain-Derived Neurotrophic Factor Content in EAE Rat Model Experimental objective: neurotrophic factors are important substances for constituting nerve regeneration microenvironment. Brain-derived neurotrophic factor (BDNF) is an important neurotrophic factor, can promote the regeneration and plerosis of myelin sheath. In this experiment, BDNF content of spinal cord lumbar intumescentia in EAE rat model was measured by immunohistochemical method, and the effects of Epimedium flavanoids on the content was observed.

Experimental method: the rats were anesthetized with 10% chloral hydrate, fixed by perfusion of 4% paraformaldehyde, spinal cord tissues were taken for frozen section. Incubated with BDNF primary antibody, added with corresponding secondary antibody and third antibody, DAB colorated, observed under microscope, and pictures were analyzed using Image Pro plus5.0 software.

Experimental results: the total area of BDNF positive cells and integrated optical density (IOD) were analyzed by software, the BDNF expression of spinal cord lumbar intumescentia in EAE rat model was significantly lower than that of the normal control group; while the expression of BDNF in Epimedium flavanoids groups increased significantly (Table 16), which indicated that Epimedium flavanoids could significantly increase neurotrophic factors, improve nerve regeneration microenvironment, and facilitate the regeneration and plerosis of myelin sheath.

TABLE 16

Effects of Epimedium flavanoids on BDNF expression of spinal cord lumbar intumescentia in EAE rat model

| Group | Animal number | total area of BDNF positive cell (×10$^5$) | integrated optical density of BDNF positive cell (×10$^5$) |
|---|---|---|---|
| Normal control | 3 | 9.73 ± 0.82 | 3.42 ± 0.32 |
| EAE model | 3 | 6.97 ± 0.67$^{\#}$ | 3.07 ± 0.24 |
| EAE + prednisone acetate (positive control drug) | 3 | 9.43 ± 1.12* | 3.64 ± 0.23 |
| EAE + Epimedium flavanoids 20 mg/kg | 3 | 9.98 ± 0.96* | 3.60 ± 0.28 |
| EAE + Epimedium flavanoids 60 mg/kg | 3 | 11.58 ± 0.77** | 4.15 ± 0.19** |

Average value ± SD;
$^{\#\#}$P < 0.01, comparing model group with normal control group,
*P < 0.05,
**P < 0.01, comparing drug group with model group.

In sum, icariin, Epimedium flavanoids showed significant effects in many animal models on alleviating nervous system myelinoclasis and inflammatory cell infiltration, inhibiting inflammatory reaction, combating oxidative stress, increasing oligodendroglial cells to facilitate myelinization, increasing neurotrophic factors to promote the regeneration and plerosis of nerve cells and myelin sheath, and increasing peripheral blood CD4+ T cell number, reducing CD8+ T cell number, and thus could be used for prophylaxis and treatment of central and peripheral nervous system demyelinating disease caused by various reasons.

Although the specific models for carrying out the present invention are described in details, those skilled in the art would understand that various modifications and replacements of these details can be made according to the prior art, and all these changes fall within the protection of the present invention. The whole protection scope of the present invention is determined by the attached claims and any equivalents thereof.

What is claimed is:

1. A method for alleviating or repairing a disease and/or disorder associated with a nervous system myelin sheath lesion, comprising administering icariin to a patient in need thereof:
    further comprising any one of the following items a) to b):
    a) the disease and/or disorder associated with nervous system myelin sheath lesion is selected from: optical neuromyelitis, acute disseminated encephalomyelitis, diffuse sclerosis, concentric circle sclerosis, central pontine myelinolysis, acute inflammatory demyelinating polyneuropathy, and chronic inflammatory demyelinating polyneuropathy; or
    b) the disease and/or disorder associated with nervous system myelin sheath lesion is selected from: subacute combined degeneration caused by nutrition deficiency diseases, subacute sclerosing panencephalitis caused by viral infection or progressive multifocal leukoencephalopathy, and diabetic neuropathy;
    wherein icariin is administered in amounts from 0.1 µg to 250 mg per kilogram bodyweight per day.

2. The method of claim 1, wherein the icariin is administered orally.

3. The method of claim 1, wherein the icariin is administered intravenously.

4. The method of claim 1, wherein the icariin is administered intranasally.

5. The method of claim 1, wherein the icariin is administered intraperitoneally.

6. The method of claim 1, wherein the icariin is administered subcutaneously.

7. The method of claim 1, wherein the icariin is administered intramuscularly.

8. The method of claim 1, wherein the icariin is administered topically.

9. The method of claim 1, wherein the icariin is administered as a suppository.

10. A method for alleviating or repairing a disease and/or disorder associated with a nervous system myelin sheath lesion, comprising administering icariin to a patient in need thereof:
    further comprising any one of the following items a) to b):
    a) the disease and/or disorder associated with nervous system myelin sheath lesion is selected from: optical neuromyelitis, acute disseminated encephalomyelitis, diffuse sclerosis, concentric circle sclerosis, central pontine myelinolysis, acute inflammatory demyelinating polyneuropathy, and chronic inflammatory demyelinating polyneuropathy; or
    b) the disease and/or disorder associated with nervous system myelin sheath lesion is selected from: subacute combined degeneration caused by nutrition deficiency diseases, subacute sclerosing panencephalitis caused by viral infection or progressive multifocal leukoencephalopathy, and diabetic neuropathy,
    wherein the icariin is administered in a pharmaceutical composition comprising from 0.01 µg to 2000 mg icariin per 100 g pharmaceutical composition and a pharmaceutically acceptable carrier.

11. A method for alleviating or repairing a disease and/or disorder associated with a nervous system myelin sheath lesion, comprising administering an epimedium flavonoid comprising from 50 to 90 wt. % icariin to a patient in need thereof:
    further comprising any one of the following items a) to b):
    a) the disease and/or disorder associated with nervous system myelin sheath lesion is selected from: optical neuromyelitis, acute disseminated encephalomyelitis, diffuse sclerosis, concentric circle sclerosis, central pontine myelinolysis, acute inflammatory demyelinating polyneuropathy, and chronic inflammatory demyelinating polyneuropathy; or
    b) the disease and/or disorder associated with nervous system myelin sheath lesion is selected from: subacute combined degeneration caused by nutrition deficiency diseases, subacute sclerosing panencephalitis caused by viral infection or progressive multifocal leukoencephalopathy, and diabetic neuropathy;
    wherein icariin is administered in amounts from 0.1 µg to 250 mg per kilogram bodyweight per day.

* * * * *